United States Patent
Friedlander et al.

(10) Patent No.: US 7,809,660 B2
(45) Date of Patent: Oct. 5, 2010

(54) SYSTEM AND METHOD TO OPTIMIZE CONTROL COHORTS USING CLUSTERING ALGORITHMS

(75) Inventors: Robert R. Friedlander, Southbury, CT (US); Richard A. Hennessy, Austin, TX (US); James R. Kraemer, Santa Fe, NM (US); John Baxter Rollins, Southlake, TX (US)

(73) Assignee: International Business Machines Corporation, Armonk, NY (US)

( * ) Notice: Subject to any disclaimer, the term of this patent is extended or adjusted under 35 U.S.C. 154(b) by 1037 days.

(21) Appl. No.: 11/542,397

(22) Filed: Oct. 3, 2006

(65) Prior Publication Data

US 2008/0082356 A1     Apr. 3, 2008

(51) Int. Cl.
    *G06N 5/00*      (2006.01)
(52) U.S. Cl. ........................................ 706/45
(58) Field of Classification Search ............ 706/45; 435/6
See application file for complete search history.

(56) References Cited

U.S. PATENT DOCUMENTS

| | | | |
|---|---|---|---|
| 4,890,227 A | 12/1989 | Watanabe et al. | |
| 5,070,453 A | 12/1991 | Duffany | |
| 5,128,871 A | 7/1992 | Schmitz | |
| 5,550,021 A * | 8/1996 | Blum et al. ............ | 435/6 |
| 5,764,740 A | 6/1998 | Holender | |
| 5,838,918 A | 11/1998 | Prager et al. | |
| 5,880,598 A | 3/1999 | Duong | |
| 6,021,403 A | 2/2000 | Horvitz et al. | |
| 6,076,166 A | 6/2000 | Moshfeghi et al. | |
| 6,212,524 B1 | 4/2001 | Weissman et al. | |
| 6,321,207 B1 | 11/2001 | Ye | |
| 6,484,155 B1 | 11/2002 | Kiss et al. | |
| 6,506,384 B1 * | 1/2003 | Laal et al. ............ | 424/168.1 |
| 6,675,159 B1 | 1/2004 | Lin et al. | |
| 6,905,816 B2 | 6/2005 | Jacobs et al. | |
| 6,937,147 B2 | 8/2005 | Dilbeck et al. | |
| 6,954,736 B2 | 10/2005 | Menninger et al. | |
| 7,179,645 B2 * | 2/2007 | Humphreys et al. ...... | 435/320.1 |
| 7,181,428 B2 | 2/2007 | Lawrence | |
| 7,213,009 B2 * | 5/2007 | Pestotnik et al. | |
| 7,295,925 B2 | 11/2007 | Breed et al. | |
| 7,403,922 B1 | 7/2008 | Lewis et al. | |
| 2002/0052756 A1 | 5/2002 | Lomangino | |
| 2002/0111922 A1 | 8/2002 | Young et al. | |
| 2003/0140063 A1 | 7/2003 | Pizzorno et al. | |
| 2003/0177038 A1 | 9/2003 | Rao | |

(Continued)

OTHER PUBLICATIONS

Kiang, M, Extending the Kohonen self-organizing map networks for clustering analysis, Computational Statistics & Data Analysis, vol. 38, 2001, pp. 161-180.*

(Continued)

*Primary Examiner*—Wilbert L Starks, Jr.
(74) *Attorney, Agent, or Firm*—Yee & Associates, P.C.; John R. Pivnichny

(57) ABSTRACT

A computer implemented method, apparatus, and computer usable program code for automatically selecting an optimal control cohort. Attributes are selected based on patient data. Treatment cohort records are clustered to form clustered treatment cohorts. Control cohort records are scored to form potential control cohort members. The optimal control cohort is selected by minimizing differences between the potential control cohort members and the clustered treatment cohorts.

20 Claims, 5 Drawing Sheets

U.S. PATENT DOCUMENTS

| | | | |
|---|---|---|---|
| 2004/0006694 | A1 | 1/2004 | Heelan et al. |
| 2004/0122787 | A1 | 6/2004 | Avinash et al. |
| 2005/0004823 | A1 | 1/2005 | Hnatio |
| 2005/0038608 | A1 | 2/2005 | Chandra et al. |
| 2005/0144062 | A1 | 6/2005 | Mittal et al. |
| 2005/0149466 | A1 | 7/2005 | Hale et al. |
| 2005/0165594 | A1 | 7/2005 | Chandra et al. |
| 2006/0036560 | A1 | 2/2006 | Fogel |
| 2006/0069514 | A1* | 3/2006 | Chow et al. |
| 2006/0155627 | A1 | 7/2006 | Horowitz |
| 2006/0200435 | A1 | 9/2006 | Flinn et al. |
| 2007/0073654 | A1* | 3/2007 | Chow et al. |
| 2007/0073754 | A1* | 3/2007 | Friedlander et al. |
| 2007/0174090 | A1* | 7/2007 | Friedlander et al. |
| 2007/0174091 | A1* | 7/2007 | Friedlander et al. |
| 2007/0185737 | A1* | 8/2007 | Friedlander et al. |
| 2007/0203872 | A1 | 8/2007 | Flinn et al. |
| 2007/0244701 | A1* | 10/2007 | Erlanger et al. |
| 2007/0274337 | A1 | 11/2007 | Purpura |
| 2007/0276851 | A1* | 11/2007 | Friedlander et al. |
| 2008/0015871 | A1 | 1/2008 | Eder |
| 2008/0065576 | A1 | 3/2008 | Friedlander et al. |
| 2008/0077463 | A1 | 3/2008 | Friedlander et al. |
| 2008/0082374 | A1 | 4/2008 | Kennis et al. |
| 2008/0114779 | A1 | 5/2008 | Friedlander et al. |
| 2008/0172352 | A1 | 7/2008 | Friedlander et al. |
| 2008/0177687 | A1 | 7/2008 | Friedlander et al. |
| 2008/0177688 | A1 | 7/2008 | Friedlander et al. |
| 2008/0208801 | A1 | 8/2008 | Friedlander et al. |
| 2008/0208813 | A1 | 8/2008 | Friedlander et al. |
| 2008/0208814 | A1 | 8/2008 | Friedlander et al. |
| 2008/0208832 | A1 | 8/2008 | Friedlander et al. |
| 2008/0208838 | A1 | 8/2008 | Friedlander et al. |
| 2008/0208875 | A1 | 8/2008 | Friedlander et al. |
| 2008/0208901 | A1 | 8/2008 | Friedlander et al. |
| 2008/0208902 | A1 | 8/2008 | Friedlander et al. |
| 2008/0208903 | A1 | 8/2008 | Friedlander et al. |
| 2008/0208904 | A1 | 8/2008 | Friedlander et al. |

OTHER PUBLICATIONS

Johansson, et al., Visual Analysis based on Algorithmic Classification, Proceedings of the Seventh International Conference on Information Visualization, 2003, pp. 1-8.*

Hashemi et al, Development of Group's Signature for Evaluation of Skin Cancer in Mice Caused by Ultraviolet Radiation, Proceedings of the International Conference on Information Technology: Computers and Communications (ITCC '03), 2003, pp. 1-4.*

Beaglehole, R, Men Ageing and Health: Achieving health across the life span, 2nd World Congress on the Ageing Male, World Health Organization, Feb. 2000, pp. 1-63.*

Hashemi et al, Development of Group's Signature for Evaluation of Skin Cancer in Mice Caused by Ultraviolet Radiation, Proceedings of the International Conference on Information Technology: Computers and Communications (ITCC '03), 2003, pp. 1-4.*

Beaglehole, R, Men Ageing and Health: Achieving health across the life span, 2nd World Congress on the Ageing Male, World Health Organization, Feb. 2000, pp. 1-63.*

Hayes et al., "Picking Up the Pieces: Utilizing Disaster Recovery Project Management to Improve Readiness and Response Time", IEEE Industry Applications Magazine, Nov./Dec. 2002, pp. 1-10.

Wang et al., "A Mathematical Approach to Disaster Recovery Planning", Xidian University, National Info Security Engineering and Technology Research Center, Beijing, China, Proceedings of the First International Conference of Semantics, Knowledge, and Grid, SKG 2005, pp. 1-3.

Silver, E.A., "An Overview of Heuristic Solution Methods", The Journal of the Operational Research Society, vol. 55, No. 9, Sep. 2004, pp. 936-956.

Chen et al., "Research on Organization Method of Development Activities for Complicated Product", The 9th International Conference on Computer Supported Cooperative Work in Design Proceedings, vol. 1, May 24-26, 2005, pp. 234-239.

Cao et al., "Research on Resource Scheduling for Development Process of Complicated Product", The 9th International Conference on Computer Supported Cooperative Work in Design Proceedings, vol. 1, May 24-26, 2005, pp. 229-331.

Altmann et al., "Cooperative Software Development: Concepts, Model and Tools", C Doppler Laboratory for Software Engineering, Johannes Kepler University, Linz, 1999, pp. 194-207.

Souder, William E., "Analytical Effectiveness of Mathematical Models for R&D Project Selection", Management Science, Application Series, vol. 19, No. 8, Apr. 1973, pp. 907-923.

U.S. Appl. No. 11/516,954, filed Sep. 7, 2006, Friedlander et al.
U.S. Appl. No. 11/874,382, filed Oct. 18, 2007, Friedlander et al.
U.S. Appl. No. 12/130,779, filed May 30, 2008, Friedlander et al.
U.S. Appl. No. 12/121,947, filed May 16, 2008, Angell et al.
U.S. Appl. No. 12/135,972, filed Jun. 9, 2008, Angell et al.
U.S. Appl. No. 12/135,960, filed Jun. 9, 2008, Angell et al.
U.S. Appl. No. 12/243,825, filed Oct. 1, 2008, Angell et al.

Luckham et al., "Event Processing Glossary", May 2008, Retrieved Jun. 9, 2008, pp. 1-13, <http://complexevents.com/?p=361>.*

"AHRQ Quality Indicators—Patient Safety Indicators—Technical Specifications", Department of Health and Human Services Agency for Healthcare Research and Quality, Version 3.1, Mar. 12, 2007, pp. 1-107, <http://www.qualityindicators.ahrq.gov>.*

* cited by examiner

SYSTEM AND METHOD TO OPTIMIZE CONTROL COHORTS USING CLUSTERING ALGORITHMS

BACKGROUND OF THE INVENTION

1. Field of the Invention

The present invention relates generally to selecting control cohorts and more particularly, to a computer implemented method, apparatus, and computer usable program code for automatically selecting a control cohort.

2. Description of the Related Art

A cohort is a group of individuals, machines, components, or modules identified by a set of one or more common characteristics. This group is studied over a period of time as part of a scientific study. A cohort may be studied for medical treatment, engineering, manufacturing, or for any other scientific purpose. A treatment cohort is a cohort selected for a particular action or treatment.

A control cohort is a group selected from a population that is used as the control. The control cohort is observed under ordinary conditions while another group is subjected to the treatment or other factor being studied. The data from the control group is the baseline against which all other experimental results must be measured. For example, a control cohort in a study of medicines for colon cancer may include individuals selected for specified characteristics, such as gender, age, physical condition, or disease state that do not receive the treatment.

The control cohort is used for statistical and analytical purposes. Particularly, the control cohorts are compared with action or treatment cohorts to note differences, developments, reactions, and other specified conditions. Control cohorts are heavily scrutinized by researchers, reviewers, and others that may want to validate or invalidate the viability of a test, treatment, or other research. If a control cohort is not selected according to scientifically accepted principles, an entire research project or study may be considered of no validity wasting large amounts of time and money. In the case of medical research, selection of a less than optimal control cohort may prevent proving the efficacy of a drug or treatment or incorrectly rejecting the efficacy of a drug or treatment. In the first case, billions of dollars of potential revenue may be lost. In the second case, a drug or treatment may be necessarily withdrawn from marketing when it is discovered that the drug or treatment is ineffective or harmful leading to losses in drug development, marketing, and even possible law suits.

Control cohorts are typically manually selected by researchers. Manually selecting a control cohort may be difficult for various reasons. For example, a user selecting the control cohort may introduce bias. Justifying the reasons, attributes, judgment calls, and weighting schemes for selecting the control cohort may be very difficult. Unfortunately, in many cases, the results of difficult and prolonged scientific research and studies may be considered unreliable or unacceptable requiring that the results be ignored or repeated. As a result, manual selection of control cohorts is extremely difficult, expensive, and unreliable.

SUMMARY OF THE INVENTION

The illustrative embodiments provide a computer implemented method, apparatus, and computer usable program code for automatically selecting an optimal control cohort. Attributes are selected based on patient data. Treatment cohort records are clustered to form clustered treatment cohorts. Control cohort records are scored to form potential control cohort members. The optimal control cohort is selected by minimizing differences between the potential control cohort members and the clustered treatment cohorts.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
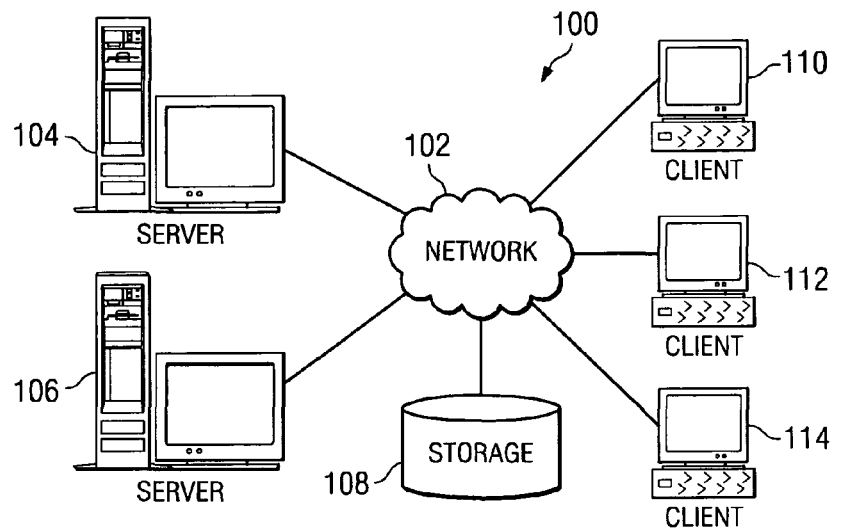
FIG. 1 is a pictorial representation of a data processing system in which an illustrative embodiment may be implemented.
Figure 2:
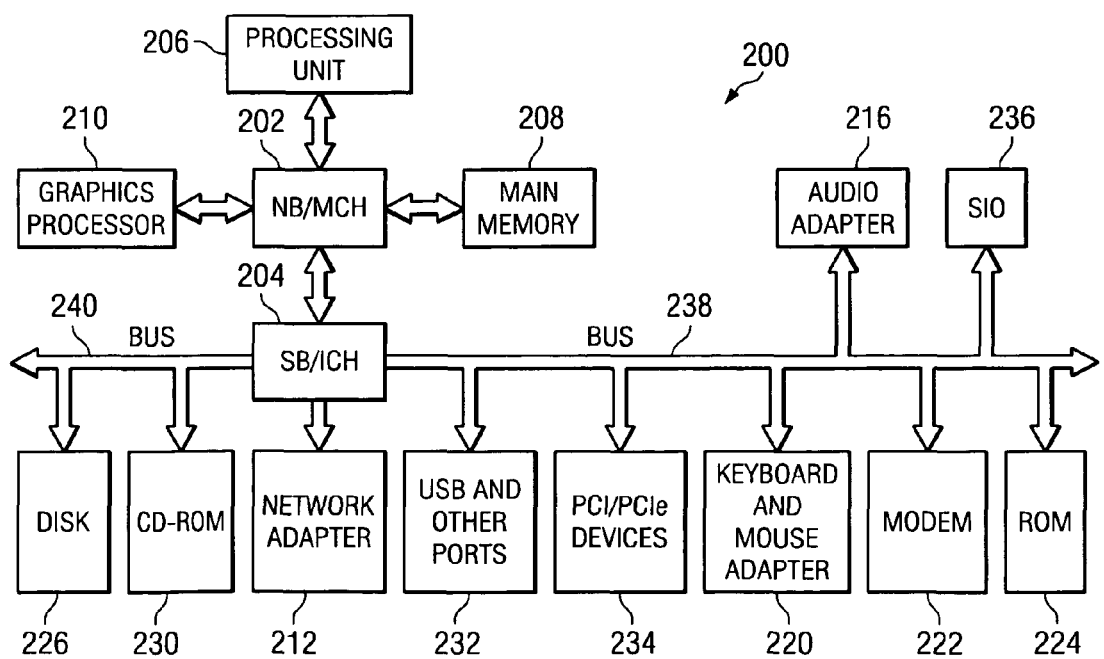
FIG. 2 is a block diagram of a data processing system in which an illustrative embodiment may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

With reference now to the figures, FIG. 1 depicts a pictorial representation of a network of data processing systems in which an illustrative embodiment may be implemented. Network data processing system 100 is a network of computers in which embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. These clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example.

Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for different embodiments.

With reference now to FIG. 2, a block diagram of a data processing system is shown in which an illustrative embodiment may be implemented. Data processing system 200 is an example of a computer, such as server 104 or client 110 in FIG. 1, in which computer usable code or instructions implementing the processes may be located for the different embodiments.

In the depicted example, data processing system 200 employs a hub architecture including a north bridge and memory controller hub (MCH) 202 and a south bridge and input/output (I/O) controller hub (ICH) 204. Processor 206, main memory 208, and graphics processor 210 are coupled to north bridge and memory controller hub 202. Graphics processor 210 may be coupled to the MCH through an accelerated graphics port (AGP), for example.

In the depicted example, local area network (LAN) adapter 212 is coupled to south bridge and I/O controller hub 204 and audio adapter 216, keyboard and mouse adapter 220, modem 222, read only memory (ROM) 224, universal serial bus (USB) ports and other communications ports 232, and PCI/PCIe devices 234 are coupled to south bridge and I/O controller hub 204 through bus 238, and hard disk drive (HDD) 226 and CD-ROM drive 230 are coupled to south bridge and I/O controller hub 204 through bus 240. PCI/PCIe devices may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM drive 230 may use, for example, an integrated drive electronics (IDE) or serial advanced technology attachment (SATA) interface. A super I/O (SIO) device 236 may be coupled to south bridge and I/O controller hub 204.

An operating system runs on processor 206 and coordinates and provides control of various components within data processing system 200 in FIG. 2. The operating system may be a commercially available operating system such as Microsoft® Windows® XP (Microsoft and Windows are trademarks of Microsoft Corporation in the United States, other countries, or both). An object oriented programming system, such as the Java™ programming system, may run in conjunction with the operating system and provides calls to the operating system from Java programs or applications executing on data processing system 200 (Java and all Java-based trademarks are trademarks of Sun Microsystems, Inc. in the United States, other countries, or both).

Instructions for the operating system, the object-oriented programming system, and applications or programs are located on storage devices, such as hard disk drive 226, and may be loaded into main memory 208 for execution by processor 206. The processes of the illustrative embodiments may be performed by processor 206 using computer implemented instructions, which may be located in a memory such as, for example, main memory 208, read only memory 224, or in one or more peripheral devices.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course the bus system may be implemented using any type of communications fabric or architecture that provides for a transfer of data between different components or devices attached to the fabric or architecture. A communications unit may include one or more devices used to transmit and receive data, such as a modem or a network adapter. A memory may be, for example, main memory 208 or a cache such as found in north bridge and memory controller hub 202. A processing unit may include one or more processors or CPUs. The depicted examples in FIGS. 1-2 and above-described examples are not meant to imply architectural limitations. For example, data processing system 200 also may be a tablet computer, laptop computer, or telephone device in addition to taking the form of a PDA.

The illustrative embodiments provide a computer implemented method, apparatus, and computer usable program code for optimizing control cohorts. Results of a clustering process are used to calculate an objective function for selecting an optimal control cohort. A cohort is a group of individuals with common characteristics. Frequently, cohorts are used to test the effectiveness of medical treatments. Treatments are processes, medical procedures, drugs, actions, lifestyle changes, or other treatments prescribed for a specified purpose. A control cohort is a group of individuals that share a common characteristic that does not receive the treatment. The control cohort is compared against individuals or other cohorts that received the treatment to statistically prove the efficacy of the treatment.

The illustrative embodiments provide an automated method, apparatus, and computer usable program code for selecting individuals for a control cohort. To demonstrate a cause and effect relationship, an experiment must be designed to show that a phenomenon occurs after a certain treatment is given to a subject and that the phenomenon does not occur in the absence of the treatment. A properly designed experiment generally compares the results obtained from a treatment cohort against a control cohort which is selected to be practically identical. For most treatments, it is often preferable that the same number of individuals is selected for both the treatment cohort and the control cohort for comparative accuracy. The classical example is a drug trial. The cohort or group receiving the drug would be the treatment cohort, and the group receiving the placebo would be the control cohort. The difficulty is in selecting the two cohorts to be as near to identical as possible while not introducing human bias.

The illustrative embodiments provide an automated method, apparatus, and computer usable program code for selecting a control cohort. Because the features in the different embodiments are automated, the results are repeatable and introduce minimum human bias. The results are independently verifiable and repeatable in order to scientifically certify treatment results.

Figure 3:
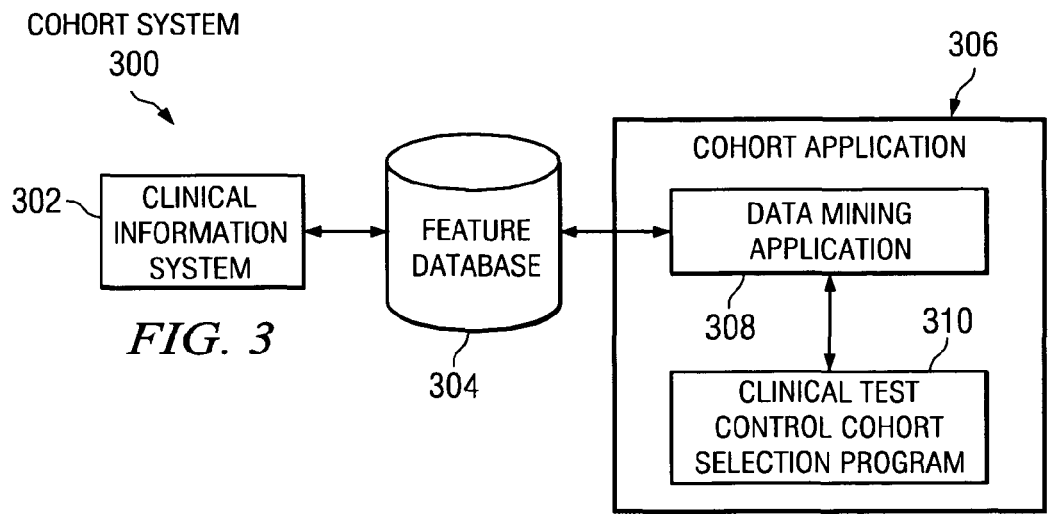
FIG. 3 is a block diagram of a system for generating control cohorts in accordance with an illustrative embodiment.

FIG. 3 is a block diagram of a system for generating control cohorts in accordance with an illustrative embodiment. Cohort system 300 is a system for generating control cohorts. Cohort system 300 includes clinical information system (CIS) 302, feature database 304, and cohort application 306. Each component of cohort system 300 may be interconnected via a network, such as network 102 of FIG. 1. Cohort application 306 further includes data mining application 308 and clinical test control cohort selection program 310.

Clinical information system 302 is a management system for managing patient data. This data may include, for example, demographic data, family health history data, vital signs, laboratory test results, drug treatment history, admission-discharge-treatment (ADT) records, co-morbidities, modality images, genetic data, and other patient data. Clinical information system 302 may be executed by a computing device, such as server 104 or client 110 of FIG. 1. Clinical information system 302 may also include information about population of patients as a whole. Such information may disclose patients who have agreed to participate in medical research but who are not participants in a current study. Clinical information system 302 includes medical records for acquisition, storage, manipulation, and distribution of clinical information for individuals and organizations. Clinical information system 302 is scalable, allowing information to expand as needed. Clinical information system 302 may also include information sourced from pre-existing systems, such as pharmacy management systems, laboratory management systems, and radiology management systems.

Feature database 304 is a database in a storage device, such as storage 108 of FIG. 1. Feature database 304 is populated with data from clinical information system 302. Feature database 304 includes patient data in the form of attributes. Attributes define features, variables, and characteristics of each patient. The most common attributes may include gender, age, disease or illness, and state of the disease.

Cohort application 306 is a program for selecting control cohorts. Cohort application 306 is executed by a computing device, such as server 104 or client 110 of FIG. 1. Data mining application 308 is a program that provides data mining functionality on feature database 304 and other interconnected databases. In one example, data mining application 308 may be a program, such as DB2 Intelligent Miner produced by International Business Machines Corporation. Data mining is the process of automatically searching large volumes of data for patterns. Data mining may be further defined as the nontrivial extraction of implicit, previously unknown, and potentially useful information from data. Data mining application 308 uses computational techniques from statistics, information theory, machine learning, and pattern recognition.

Particularly, data mining application 308 extracts useful information from feature database 304. Data mining application 308 allows users to select data, analyze data, show patterns, sort data, determine relationships, and generate statistics. Data mining application 308 may be used to cluster records in feature database 304 based on similar attributes. Data mining application 308 searches the records for attributes that most frequently occur in common and groups the related records or members accordingly for display or analysis to the user. This grouping process is referred to as clustering. The results of clustering show the number of detected clusters and the attributes that make up each cluster. Clustering is further described with respect to FIGS. 4A-4B.

For example, data mining application 308 may be able to group patient records to show the effect of a new sepsis blood infection medicine. Currently, about 35 percent of all patients with the diagnosis of sepsis die. Patients entering an emergency department of a hospital who receive a diagnosis of sepsis, and who are not responding to classical treatments, may be recruited to participate in a drug trial. A statistical control cohort of similarly ill patients could be developed by cohort system 300, using records from historical patients, patients from another similar hospital, and patients who choose not to participate. Potential features to produce a clustering model could include age, co-morbidities, gender, surgical procedures, number of days of current hospitalization, O2 blood saturation, blood pH, blood lactose levels, bilirubin levels, blood pressure, respiration, mental acuity tests, and urine output.

Data mining application 308 may use a clustering technique or model known as a Kohonen feature map neural network or neural clustering. Kohonen feature maps specify a number of clusters and the maximum number of passes through the data. The number of clusters must be between one and the number of records in the treatment cohort. The greater the number of clusters, the better the comparisons can be made between the treatment and the control cohort. Clusters are natural groupings of patient records based on the specified features or attributes. For example, a user may request that data mining application 308 generate eight clusters in a maximum of ten passes. The main task of neural clustering is to find a center for each cluster. The center is also called the cluster prototype. Scores are generated based on the distance between each patient record and each of the cluster prototypes. Scores closer to zero have a higher degree of similarity to the cluster prototype. The higher the score, the more dissimilar the record is from the cluster prototype.

All inputs to a Kohonen feature map must be scaled from 0.0 to 1.0. In addition, categorical values must be converted into numeric codes for presentation to the neural network. Conversions may be made by methods that retain the ordinal order of the input data, such as discrete step functions or bucketing of values. Each record is assigned to a single cluster, but by using data mining application 308, a user may determine a record's Euclidean dimensional distance for all cluster prototypes. Clustering is performed for the treatment cohort. Clinical test control cohort selection program 310 minimizes the sum of the Euclidean distances between the individuals or members in the treatment cohorts and the control cohort. Clinical test control cohort selection program 310 may incorporate an integer programming model, such as integer programming system 806 of FIG. 8. This program may be programmed in International Business Machine Corporation products, such as Mathematical Programming System extended (MPSX), the IBM Optimization Subroutine Library, or the open source GNU Linear Programming Kit. The illustrative embodiments minimize the summation of all records/cluster prototype Euclidean distances from the potential control cohort members to select the optimum control cohort.

Figure 4A:
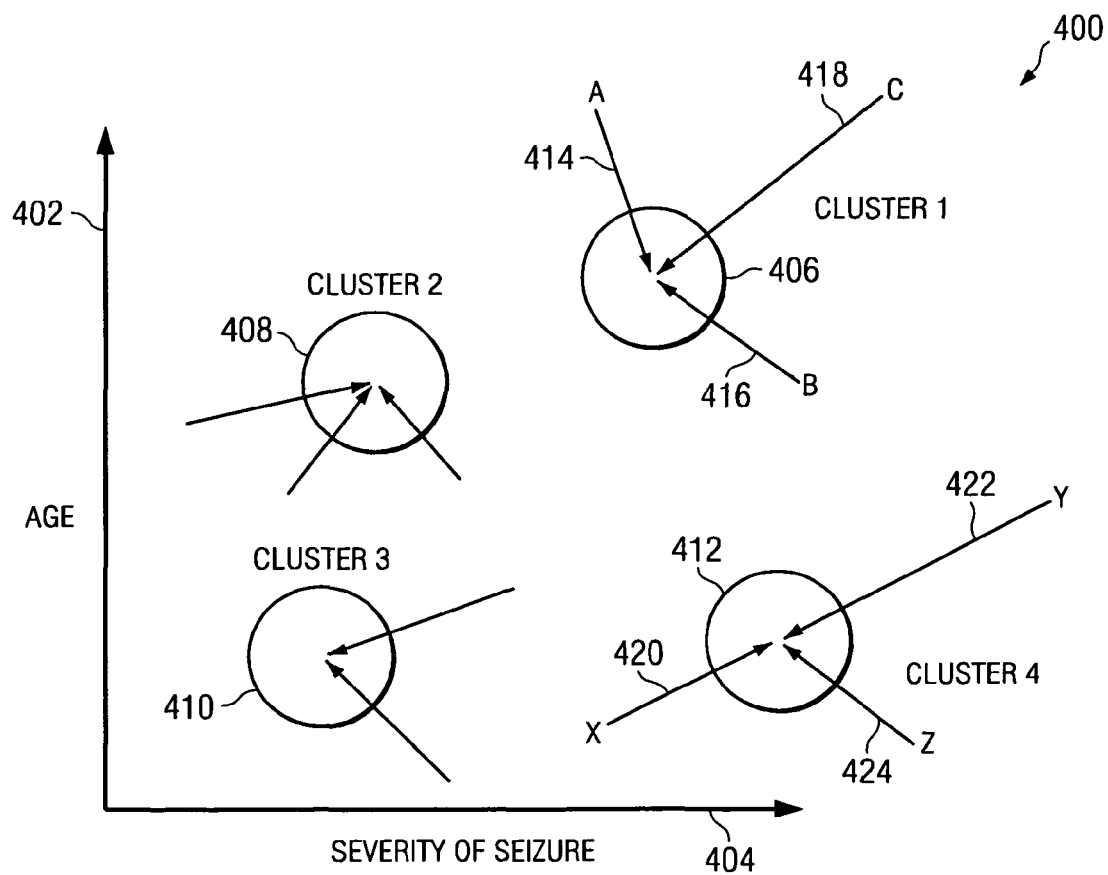
FIGS. 4A-4B are graphical illustrations of clustering in accordance with an illustrative embodiment.
Figure 4B:
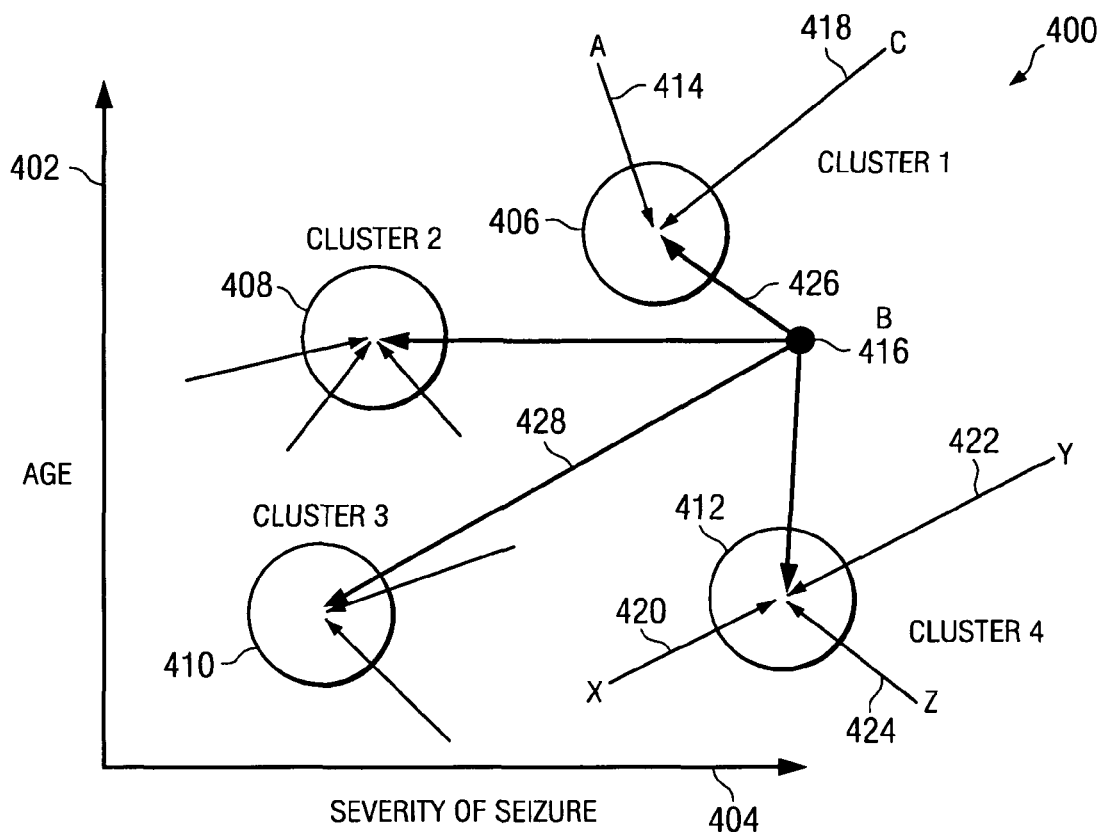

FIGS. 4A-4B are graphical illustrations of clustering in accordance with an illustrative embodiment. Feature map 400 of FIG. 4A is a self-organizing map (SOM) and is a subtype of artificial neural networks. Feature map 400 is trained using unsupervised learning to produce low-dimensional representation of the training samples while preserving the topological properties of the input space. This makes feature map 400 especially useful for visualizing high-dimensional data, including cohorts and clusters.

In one illustrative embodiment, feature map 400 is a Kohonen Feature Map neural network. Feature map 400 uses a process called self-organization to group similar patient records together. Feature map 400 may use various dimensions. In this example, feature map 400 is a two-dimensional feature map including age 402 and severity of seizure 404. Feature map 400 may include as many dimensions as there are features, such as age, gender, and severity of illness. Feature map 400 also includes cluster 1 406, cluster 2 408, cluster 3 410, and cluster 4 412. The clusters are the result of using feature map 400 to group individual patients based on the features. The clusters are self-grouped local estimates of all data or patients being analyzed based on competitive learning. When a training sample of patients is analyzed by data mining application 308 of FIG. 3, each patient is grouped into clusters where the clusters are weighted functions that best represent natural divisions of all patients based on the specified features.

The user may choose to specify the number of clusters and the maximum number of passes through the data. These parameters control the processing time and the degree of granularity used when patient records are assigned to clusters. The primary task of neural clustering is to find a center for each cluster. The center is called the cluster prototype. For each record in the input patient data set, the neural clustering data mining algorithm computes the cluster prototype that is the closest to the records. For example, patient record A 414, patient record B 416, and patient record C 418 are grouped into cluster 1 406. Additionally, patient record X 420, patient record Y 422, and patient record Z 424 are grouped into cluster 4 412.

FIG. 4B further illustrates how the score for each data record is represented by the Euclidean distance from the cluster prototype. The higher the score, the more dissimilar the record is from the particular cluster prototype. With each pass over the input patient data, the centers are adjusted so that a better quality of the overall clustering model is reached. To score a potential control cohort for each patient record, the Euclidian distance is calculated from each cluster prototype. This score is passed along to an integer programming system in clinical test control cohort selection program 310 of FIG. 3. The scoring of each record is further shown by integer programming system 806 of FIG. 8 below.

For example, patient B 416 is scored into the cluster prototype or center of cluster 1 406, cluster 2 408, cluster 3 410 and cluster 4 412. A Euclidean distance between patient B 416 and cluster 1 406, cluster 2 408, cluster 3 410 and cluster 4 412 is shown. In this example, distance 1 426, separating patient B 416 from cluster 1 406, is the closest. Distance 3 428, separating patient B 416 from cluster 3 410, is the furthest. These distances indicate that cluster 1 406 is the best fit.

Figure 5:
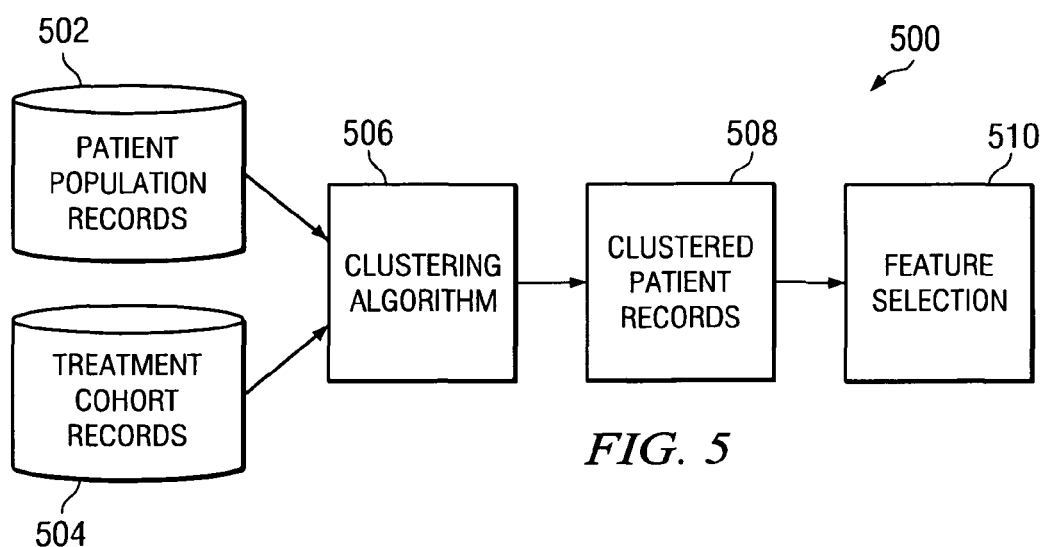
FIG. 5 is a block diagram illustrating information flow for feature selection in accordance with an illustrative embodiment.

FIG. 5 is a block diagram illustrating information flow for feature selection in accordance with an illustrative embodiment. The block diagram of FIG. 5 may be implemented in cohort application 306 of FIG. 3. Feature selection system 500 includes various components and modules used to perform variable selection. The features selected are the features or variables that have the strongest effect in cluster assignment. For example, blood pressure and respiration may be more important in cluster assignment than patient gender. Feature selection system 500 may be used to perform step 902 of FIG. 9. Feature selection system 500 includes patient population records 502, treatment cohort records 504, clustering algorithm 506, clustered patient records 508, and produces feature selection 510.

Patient population records 502 are all records for patients who are potential control cohort members. Patient population records 502 and treatment cohort records 504 may be stored in a database or system, such as clinical information system 302 of FIG. 3. Treatment cohort records 504 are all records for the selected treatment cohort. The treatment cohort is selected based on the research, study, or other test that is being performed.

Clustering algorithm 506 uses the features from treatment cohort records 504 to group patient population records in order to form clustered patient records 508. Clustered patient records 508 include all patients grouped according to features of treatment cohort records 504. For example, clustered patient records 508 may be clustered by a clustering algorithm according to gender, age, physical condition, genetics, disease, disease state, or any other quantifiable, identifiable, or other measurable attribute. Clustered patient records 508 are clustered using feature selection 510.

Feature selection 510 is the features and variables that are most important for a control cohort to mirror the treatment cohort. For example, based on the treatment cohort, the variables in feature selection 510 most important to match in the treatment cohort may be age 402 and severity of seizure 404 as shown in FIG. 4.

Figure 6:
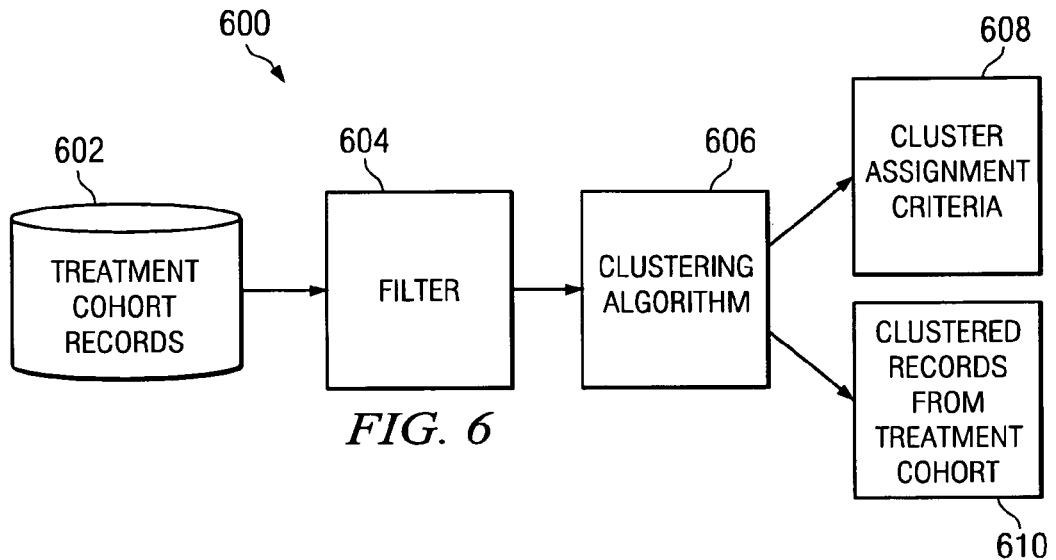
FIG. 6 is a block diagram illustrating information flow for clustering records in accordance with an illustrative embodiment.

FIG. 6 is a block diagram illustrating information flow for clustering records in accordance with an illustrative embodiment. The block diagram of FIG. 6 may be implemented in cohort application 306 of FIG. 3. Cluster system 600 includes various components and modules used to cluster assignment criteria and records from the treatment cohort. Cluster system 600 may be used to perform step 904 of FIG. 9. Cluster system 600 includes treatment cohort records 602, filter 604, clustering algorithm 606, cluster assignment criteria 608, and clustered records from treatment cohort 610. Filter 604 is used to eliminate any patient records that have significant co-morbidities that would by itself eliminate inclusion in a drug trial. Co-morbidities are other diseases, illnesses, or conditions in addition to the desired features. For example, it may be desirable to exclude results from persons with more than one stroke from the statistical analysis of a new heart drug.

Treatment cohort records 602 are the same as treatment cohort records 504 of FIG. 5. Filter 604 filters treatment cohort records 602 to include only selected variables such as those selected by feature selection 510 of FIG. 5.

Clustering algorithm 606 is similar to clustering algorithm 506 of FIG. 5. Clustering algorithm 606 uses the results from filter 604 to generate cluster assignment criteria 608 and clustered records from treatment cohort 610. For example, patient A 414, patient B 416, and patient C 418 are assigned into cluster 1 406, all of FIGS. 4A-4B. Clustered records from treatment cohort 610 are the records for patients in the treatment cohort. Every patient is assigned to a primary cluster, and a Euclidean distance to all other clusters is determined. The distance is a distance, such as distance 426, separating patient B 416 and the center or cluster prototype of cluster 1 406 of FIG. 4B. In FIG. 4B, patient B 416 is grouped into the primary cluster of cluster 1 406 because of proximity. Distances to cluster 2 408, cluster 3 410, and cluster 4 412 are also determined.

Figure 7:
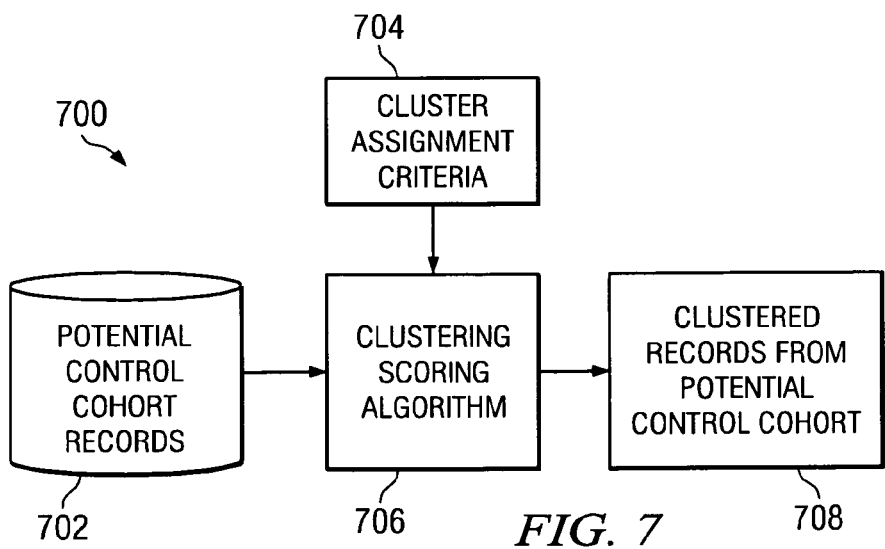
FIG. 7 is a block diagram illustrating information flow for clustering records for a potential control cohort in accordance with an illustrative embodiment.

FIG. 7 is a block diagram illustrating information flow for clustering records for a potential control cohort in accordance with an illustrative embodiment. The block diagram of FIG. 7 may be implemented in cohort application 306 of FIG. 3. Cluster system 700 includes various components and modules used to cluster potential control cohorts. Cluster system 700 may be used to perform step 906 of FIG. 9. Cluster system 700 includes potential control cohort records 702, cluster assignment criteria 704, clustering scoring algorithm 706, and clustered records from potential control cohort 708.

Potential control cohort records 702 are the records from patient population records, such as patient population records 502 of FIG. 5 that may be selected to be part of the control cohort. For example, potential control cohort records 702 do not include patient records from the treatment cohort. Clustering scoring algorithm 706 uses cluster assignment criteria 704 to generate clustered records from potential control cohort 708. Cluster assignment criteria are the same as cluster assignment criteria 608 of FIG. 6.

Figure 8:
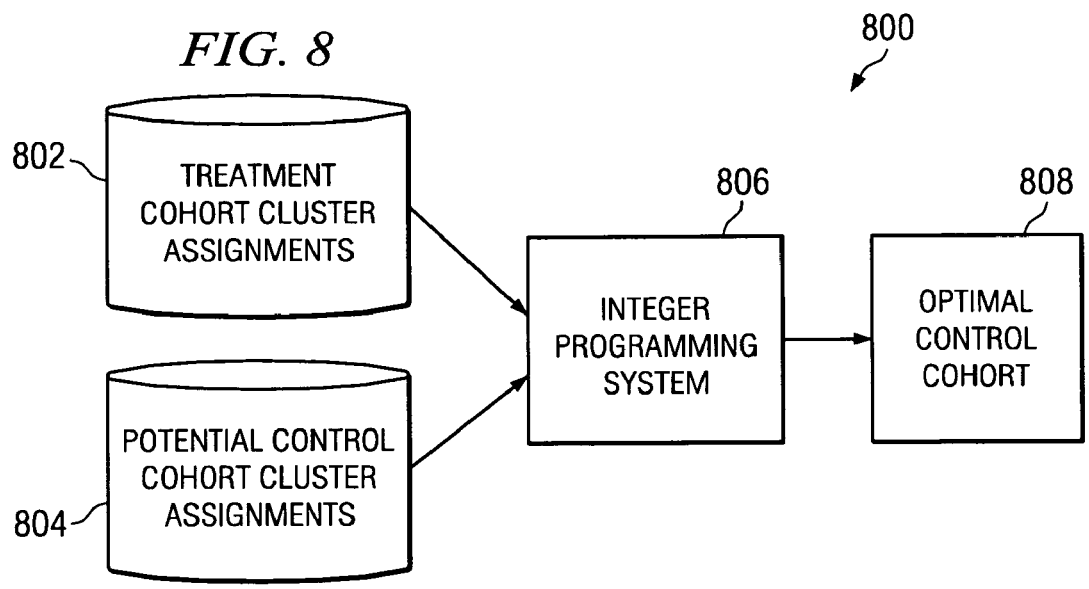
FIG. 8 is a block diagram illustrating information flow for generating an optimal control cohort in accordance with an illustrative embodiment.

FIG. 8 is a block diagram illustrating information flow for generating an optimal control cohort in accordance with an illustrative embodiment. Cluster system 800 includes various components and modules used to cluster the optimal control cohort. Cluster system 800 may be used to perform step 908 of FIG. 9. Cluster system 800 includes treatment cohort cluster assignments 802, potential control cohort cluster assignments 804, integer programming system 806, and optimal control cohort 808. The cluster assignments indicate the treatment and potential control cohort records that have been grouped to that cluster.

0-1 Integer programming is a special case of integer programming where variables are required to be 0 or 1, rather than some arbitrary integer. The illustrative embodiments use integer programming system 806 because a patient is either in the control group or is not in the control group. Integer programming system 806 selects the optimum patients for optimal control cohort 808 that minimize the differences from the treatment cohort. The objective function of integer programming system 806 is to minimize the absolute value of the sum of the Euclidian distance of all possible control cohorts compared to the treatment cohort cluster prototypes. 0-1 Integer programming typically utilizes many well-known techniques to arrive at the optimum solution in far less time than would be required by complete enumeration. Patient records may be used zero or one time in the control cohort. Optimal control cohort 808 may be displayed in a graphical format to demonstrate the rank and contribution of each feature/variable for each patient in the control cohort.

Figure 9:
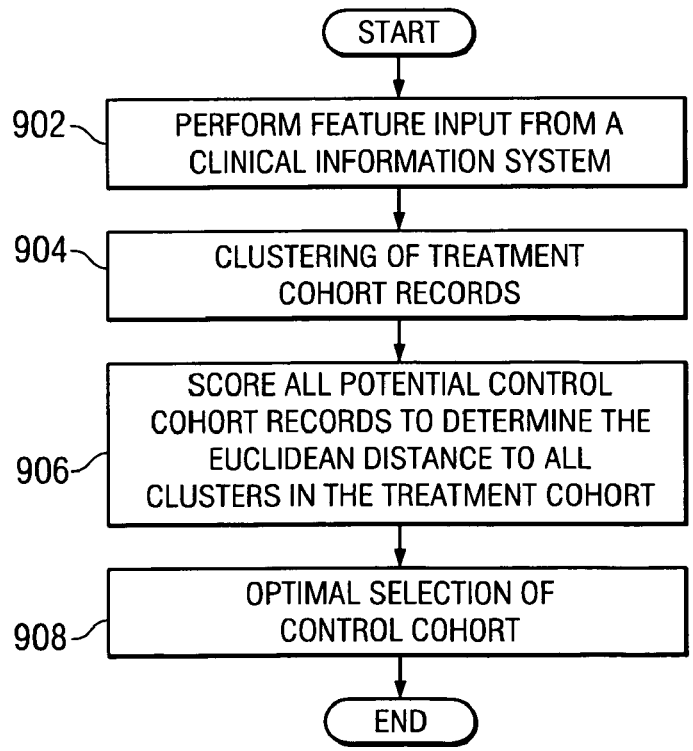
FIG. 9 is a process for optimal selection of control cohorts in accordance with an illustrative embodiment.

FIG. 9 is a flowchart of a process for optimal selection of control cohorts in accordance with an illustrative embodiment. The process of FIG. 9 may be implemented in cohort system 300 of FIG. 3. The process first performs feature input from a clinical information system (step 902). In step 902, the process step moves every potential patient feature data stored in a clinical data warehouse, such as clinical information system 302 of FIG. 3. During step 902, many more variables are input than will be used by the clustering algorithm. These extra variables will be discarded by feature selection 510 of FIG. 5.

Some variables, such as age and gender, will need to be included in all clustering models. Other variables are specific to given diseases like Gleason grading system to help describe the appearance of the cancerous prostate tissue. Most major diseases have similar scales measuring the severity and spread of a disease. In addition to variables describing the major disease focus of the disease, most patients have co-morbidities. These might be conditions like diabetes, high blood pressure, stroke, or other forms of cancer. These comorbidities may skew the statistical analysis so the control cohort must carefully select patients who well mirror the treatment cohort.

Next, the process clusters treatment cohort records (step 904). Next, the process scores all potential control cohort records to determine the Euclidean distance to all clusters in the treatment cohort (step 906). Step 904 and 906 may be performed by data mining application 308 based on data from feature database 304 and clinical information system 302 all of FIG. 3. Next, the process performs optimal selection of a control cohort (step 908) with the process terminating thereafter. Step 908 may be performed by clinical test control cohort selection program 310 of FIG. 3. The optimal selection is made based on the score calculated during step 906. The scoring may also involving weighting. For example, if a record is an equal distance between two clusters, but one of the two clusters has more records, then the record may be clustered in the cluster with more records. During step 908, names, unique identifiers, or encoded indices of individuals in the optimal control cohort are displayed or otherwise provided.

In one illustrative scenario, a new protocol has been developed to reduce the risk of re-occurrence of congestive heart failure after discharging a patient from the hospital. A pilot program is created with a budget sufficient to allow 600 patients in the treatment and control cohorts. The pilot program is designed to apply the new protocol to a treatment cohort of patients at the highest risk of re-occurrence.

The clinical selection criteria for inclusion in the treatment cohort specifies that each individual:

1. Have more than one congestive heart failure related admission during the past year.
2. Have fewer than 60 days since the last congestive heart failure related admission.
3. Be 45 years or older.

Each of these attributes may be determined during feature selection of step 902. The clinical criteria yields 296 patients for the treatment cohort, so 296 patients are needed for the control cohort. The treatment cohort and control cohort are selected from patient records stored in feature database 304 or clinical information system 302 of FIG. 3.

Originally, there were 2,927 patients available for the study. The treatment cohort reduces the patient number to 2,631 unselected patients. Next, the 296 patients of the treatment cohort are clustered during step 904. The clustering model determined during step 904 is applied to the 2,631 unselected patients to score potential control cohort records in step 906. Next, the process selects the best matching 296 patients for the optimal selection of a control cohort in step 908. The result is a group of 592 patients divided between treatment and control cohorts who best fit the clinical criteria. The results of the control cohort selection are repeatable and defendable.

Thus, the illustrative embodiments provide a computer implemented method, apparatus, and computer usable program code for optimizing control cohorts. The control cohort is automatically selected from patient records to minimize the differences between the treatment cohort and the control cohort. The results are automatic and repeatable with the introduction of minimum human bias.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for automatically selecting an optimal control cohort, the computer implemented method comprising:
   selecting attributes based on patient data;
   clustering of treatment cohort records after a co-morbidity filter is used to eliminate any patient records that include one or more co-morbidities which eliminate the patient records from inclusion in a treatment cohort record cluster to form clustered treatment cohorts;
   scoring control cohort records to form potential control cohort members; and
   selecting the optimal control cohort by minimizing differences between the potential control cohorts members and the clustered treatment cohorts.

2. The computer implemented method of claim 1, wherein the patient data is stored in a clinical database.

3. The computer implemented method of claim 1, wherein the attributes are any of features, variables, and characteristics.

4. The computer implemented method of claim 1, wherein the selecting step further comprises:
   searching the patient data to determine the attributes that most strongly differentiate assignment of patient records to particular clusters.

5. The computer implemented method of claim 1, wherein the clustered treatment cohorts show a number of clusters and characteristics of each of the number of clusters.

6. The computer implemented method of claim 1, wherein the attributes include gender, age, disease state, genetics, and physical condition.

7. The computer implemented method of claim 1, wherein each patient record is scored to calculate the Euclidean distance to all clusters.

8. The computer implemented method of claim 5, wherein a user specifies the number of clusters for the clustered treatment cohorts and a number of search passes through the patient data to generate the number of clusters specified.

9. The computer implemented method of claim 1, wherein the selecting attributes and the clustering steps are performed by a data mining application, wherein the selecting the optimal control cohort step is performed by a 0-1 integer programming model.

10. The computer implemented method of claim 1, wherein the scoring step comprises:
    scoring all patient records by computing a Euclidean distance to cluster prototypes of all treatment cohorts.

11. The computer implemented method of claim 1, further comprising:
    providing names, unique identifiers, or encoded indices of individuals in the optimal control cohort.

12. The computer implemented method of claim 1, wherein the clustering step further comprise:
    generating a feature map to form the clustered treatment cohorts.

13. The computer implemented method of claim 12, wherein the feature map is a Kohonen feature map.

14. An optimal control cohort selection system comprising:
    an attribute database operatively connected to a clinical information system for storing patient records including attributes of patients;
    a server operably connected to the attribute database wherein the server executes a data mining application and a clinical control cohort selection program wherein the data mining application selects specified attributes based on patient data, clusters treatment cohort records based on the specified attributes after a co-morbidity filter is used to eliminate any patient records that include one or more co-morbidities which eliminate the patient records from inclusion in a treatment cohort record cluster to form clustered treatment cohorts, and clusters control cohort records based on the specified attributes to form clustered control cohorts; and wherein the clinical control cohort selection program selects the optimal control cohort by minimizing differences between the clustered control cohorts and the clustered treatment cohorts.

15. The control cohort selection system of claim 14, wherein the clinical information system includes information about populations of patients wherein the information is accessed by the server.

16. The control cohort selection system of claim 14, wherein the data mining application is IBM DB2 Intelligent Miner.

17. A computer program product comprising a computer usable medium including computer usable program code for automatically selecting an optimal control cohort, the computer program product comprising:
    computer usable program code for selecting attributes based on patient data;

computer usable program code for clustering of treatment cohort records after a co-morbidity filter is used to eliminate any patient records that include one or more co-morbidities which eliminate the patient records from inclusion in a treatment cohort record cluster to form clustered treatment cohorts;

computer usable program code for scoring control cohort records to form potential control cohort members; and computer usable program code for selecting the optimal control cohort by minimizing differences between the potential control cohorts members and the clustered treatment cohorts.

18. The computer program product of claim 17, further comprising:

computer usable program code for scoring all patient records in a self organizing map by computing a Euclidean distance to cluster prototypes of all treatment cohorts; and computer usable program code for generating a feature map to form the clustered treatment cohorts.

19. The computer program product of claim 17, comprising computer usable program code for specifying a number of clusters for the clustered treatment cohorts and a number of search passes through the patient data to generate the number of clusters specified.

20. The computer program product of claim 17, wherein the computer usable program code for selecting further comprises:

computer usable program code for searching the patient data to determine the attributes that most strongly differentiate assignment of patient records to particular clusters.

* * * * *